(12) United States Patent
Bornscheuer et al.

(10) Patent No.: US 7,229,817 B2
(45) Date of Patent: Jun. 12, 2007

(54) RECOMBINANT PORCINE LIVER ESTERASES, THEIR USE AND A METHOD FOR THE PRODUCTION THEREOF

(75) Inventors: Uwe Bornscheuer, Greifswald (DE); Anna Musidlowska, Greifswald (DE); Claudia Schmidt-Dannert, Shoreview, MN (US); Stefan Lange, Stuttgart (DE)

(73) Assignee: Degussa AG, Duesseldorf (DE)

( * ) Notice: Subject to any disclaimer, the term of this patent is extended or adjusted under 35 U.S.C. 154(b) by 232 days.

(21) Appl. No.: 10/450,156

(22) PCT Filed: Dec. 6, 2001

(86) PCT No.: PCT/EP01/14338

§ 371 (c)(1),
(2), (4) Date: Feb. 24, 2004

(87) PCT Pub. No.: WO02/48322

PCT Pub. Date: Jun. 20, 2002

(65) Prior Publication Data

US 2004/0161836 A1    Aug. 19, 2004

(30) Foreign Application Priority Data

Dec. 12, 2000    (DE) ............... 100 61 864

(51) Int. Cl.
  C12N 9/18    (2006.01)
  C12N 1/20    (2006.01)
  C12N 15/00   (2006.01)
  C07H 21/04   (2006.01)

(52) U.S. Cl. ............... 435/197; 435/252.3; 435/320.1; 435/19; 536/23.2

(58) Field of Classification Search ............... 435/197, 435/19, 252.3, 320.1; 536/23.2
See application file for complete search history.

(56) References Cited

FOREIGN PATENT DOCUMENTS

WO    00 04160    1/2000

OTHER PUBLICATIONS

M. Matsushima et al.: "The nucleotide and deduced amino acid sequences of porcine liver proline- beta- naphthylamidase. Evidence for the identity with carboxylesterase" FEBS Letters, vol. 293, No. 1-2, pp. 37-41, Nov. 18, 1991.

L. David et al.: "Purification and molecular cloning of porcine intestinal glycerol-ester hydrolase-evidence for its identity with carboxylesterase" European Journal of Biochemistry, vol. 257, No. 1, pp. 142-148, Oct. 1, 1998.

J. Heim et al.: "Functional expression of a mammalian acetylcholinesterase in pichia pastorls: comparison to acetylcholinsterase, expressed and reconstituted from Escherichia coli" Biochimica et Biophysica Acta, vol. 1396, No. 3, pp. 306-319, Mar. 13, 1998.

L. Giver et al.: "Direct evolution of a thermostable esterase" Proceedings of the National Academy of Sciences of the United States of America, vol. 95, No. 22, pp. 12809-12813, Oct. 27, 1998.

Clustalw Result Clustal W (1.81) Multiple sequence alignments (2003).

S. Medda et al.: "The carboxylesterase family exhibits C-terminal sequence diversity reflecting the presence or absence of endoplasmic-reticulum-retention sequences" Eur J Biochem, vol. 206, No. 3, pp. 801-806, Jun. 15, 1992 (Abstract only).

M. Robbi et al.: "The COOH terminus of several liver caboxylesterases targets these enzymes to the lumen of the endoplasmic reticulum" J. Biol Chem, vol. 266, No. 30, pp. 20498-20503, Oct. 25, 2001 (Abstract only).

*Primary Examiner*—Tekchand Saidha
(74) *Attorney, Agent, or Firm*—Oblon, Spivak, McClelland, Maier & Neustadt, P.C.

(57) ABSTRACT

The invention relates to biotechnologically expressible, enzymically active recombinant porcine liver esterases, to a biotechnological method for the preparation thereof and to the use thereof in organic synthesis. The monomeric subunits of recombinant porcine liver esterase are truncated at their C-terminal end, compared with naturally occurring porcine liver esterase subunits. Moreover, it has proved to be an additional advantage to truncate the N-terminal end as well.

26 Claims, 5 Drawing Sheets

RECOMBINANT PORCINE LIVER ESTERASES, THEIR USE AND A METHOD FOR THE PRODUCTION THEREOF

FIELD OF THE INVENTION

The invention relates to enzymically active porcine liver esterases, to a biotechnological method for the preparation thereof and to the use thereof in organic synthesis.

DESCRIPTION OF THE RELATED ART

Lipases and esterases can be used as efficient biocatalysts for preparing a multiplicity of optically active compounds. Although quite a number of lipases, in particular those of microbial origin, are commercially available, there are, however, only very few esterases which are available for use in racemate resolution or asymmetrization.

Although it was possible to demonstrate that esterase extracts from pig liver tissue can partially convert substrates with sufficient stereoselectivity, the use of such extracts has a number of disadvantages. Apart from variations in the esterase content between various batches, the presence of further hydrolases must be regarded as a particular problem with respect to stereoselectivities (Seebach, D. et. al., Chimia (1986), 40, 315–318). There is the additional problem of conventional extracts containing a plurality of isoenzymes (Farb, D., et. al., Arch. Biochem. Biophys. (1980) 203, 214–226) some of which have substantially different substrate specificities. Heymann, E. and Junge, W. (Eur. J. Biochem. (1979), 95, 509–518; Eur. J. Biochem. (1979), 95, 519–525) carried out a complicated electrophoretic separation so that it was possible to isolate fractions which preferably cleave butyrylcholine, proline-$\beta$-naphthylamide and methyl butyrate. In contrast, other studies (e.g. Lam, L. K. P., et. al., J. Am. Chem. Soc. (1988) 110, 4409–4411) merely show differences in the activity but not specificity of individual fractions.

There is therefore a need for biotechnologically prepared porcine liver esterases of specific composition.

Although putative genes of porcine liver esterase have already been cloned successfully (Takahashi, T, et. al., J. Biol. Chem. (1989), 264, 11565–11571; FEBS Lett. (1991), 280, 297–300; FEBS Lett. (1991), 293, 37–41; Ldavid, L., et. al., Eur. J. Biochem. (1998) 257, 142–148), is has been impossible up until now to express an active porcine liver esterase functionally, despite existing demand for such enzymes.

SUMMARY OF THE INVENTION

It was therefore an object of the invention to provide an enzymically active porcine liver esterase which can be prepared biotechnologically in a simple manner.

The object was achieved by porcine liver esterases whose monomeric subunits are truncated at the C terminus, compared with the subunits of naturally occurring porcine liver esterases. Moreover, it has proved to be an additional advantage to truncate the N-terminal end as well.

DETAILED DESCRIPTION OF THE INVENTION

Figure 1:
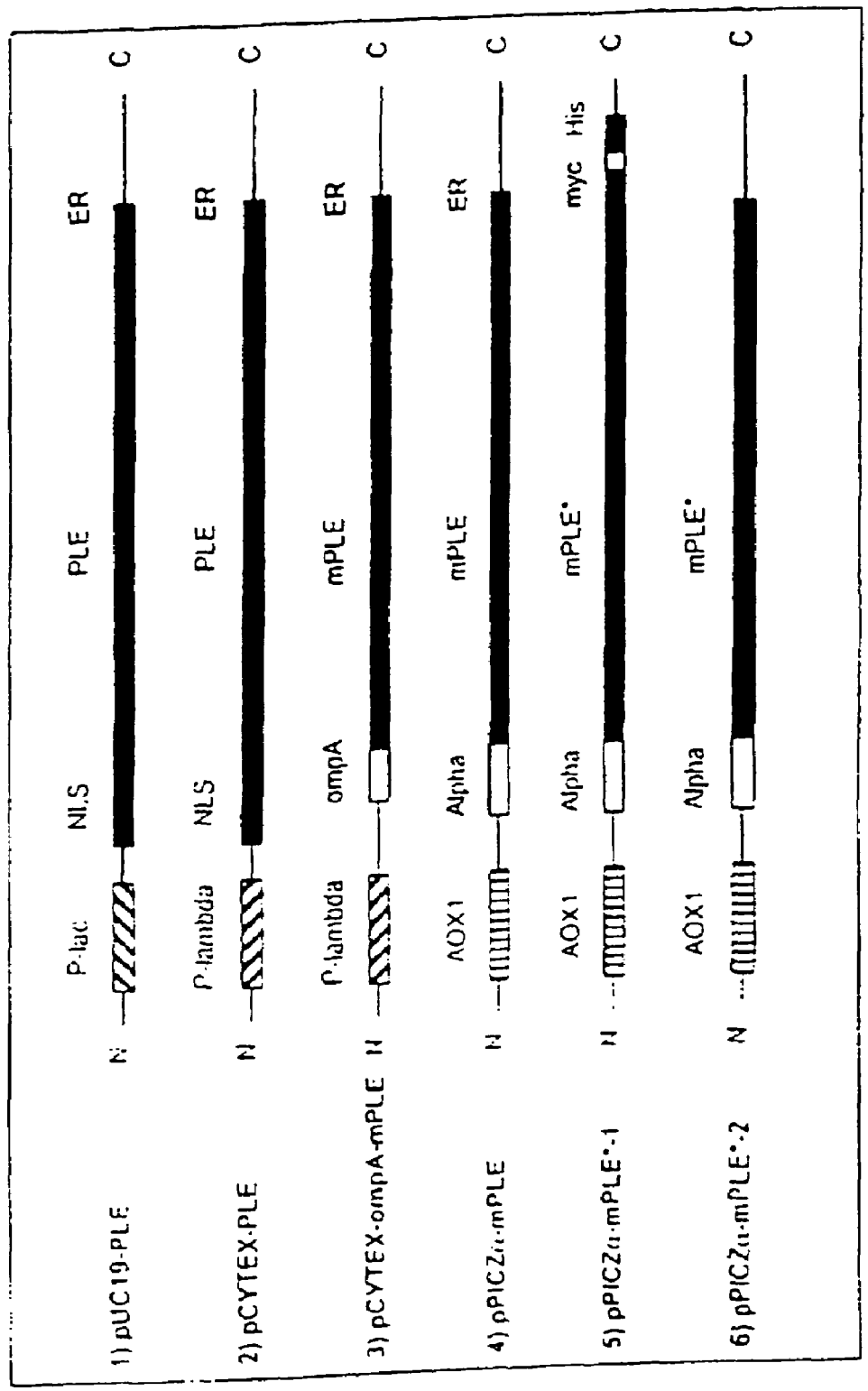
FIG. 1 depicts the vectors prepared and described in the text diagrammatically.

Surprisingly, it was possible to demonstrate that biotechnological expression with secretion of said subunits of porcine liver esterase into the medium leads to enzymically active recombinant porcine liver esterases which can be isolated essentially free of contaminations, are highly enantioselective and, on the basis of this, ensure reproducible results in substrate conversion, in particular with respect to yield and enantioselectivity.

Thus, the present invention relates to recombinant subunits of porcine liver esterases, which lack at their C-terminal end 1 to 50 amino acids, preferably 3 to 10 amino acids and particularly preferably 3 or 4 amino acids, compared with naturally occurring porcine liver esterases. The subunits of the invention may contain further functional peptide domains at the C terminus, for example myc tags and/or poly-His tags for easier isolation via affinity chromatography.

It is furthermore advantageous for the functional biotechnological preparation to remove a region of from 10 to 50 amino acids, preferably from 15 to 25 amino acids, from the N-terminal end, compared with the naturally occurring gene products.

The N terminus may likewise comprise functional peptidic domains, and in this connection secretion signal domains such as the $\alpha$-factor signal sequence, contained, for example, in the corresponding primer sequence PLE-7F (Seq. Id. No. 8), or the ompA signal sequence, contained, for example, in the primer sequence PLE-9F (Seq. Id. No. 10), are of particular interest.

Preference is given in particular to subunits of porcine liver esterases, which may be obtained starting from a putative porcine liver esterase subunit according to Swiss-Prot Acc. No. Q29550, and here especially to a porcine liver esterase subunit having the amino acid sequence Seq. Id. No. 1, to allelic forms thereof or functional mutant forms thereof whose sequences are more than 80%, in particular more than 90%, homologous and which may also be generated biotechnologically.

```
GQPASPPVVD  TAQGRVLGKY  VSLEGLAQPV  AVFLGVPFAK  PPLGSLRFAP  (Seq. Id. No. 1)

PQPAEPWSFV  KNTTSYPPMC  CQDPVVEQMT  SDLFTNGKER  LTLEFSEDCL

YLNIYTPADL  TRRGRLPVMV  WIHGGGLVLG  GAPMYDGVVL  AAHENVVVVA

IQYRLGIWGF  FSTGDEHSRG  NWGHLDQVAA  LHWVQENIAN  FGGDPGSVTI

FGESAGGESV  SVLVLSPLAK  NLFHRAISES  GVALTVALVR  KDMKAAAKQI

AVLAGCKTTT  SAVFVHCLRQ  KSEDELLDLT  LKMKFLTLDF  HGDQRESHPF

LPTVVDGVLL  PKMPEEILAE  KDFNTVPYIV  GINKQEFGWL  LPTMMGFPLS

EGKLDQKTAT  SLLWKSYPIA  NIPEELTPVA  TDKYLGGTDD  PVKKKDLFLD

LMGDVVFGVP  SVTVARQHRD  AGAPTYMYEF  QYRPSFSSDK  KPKTVIGDHG

DEIFSVFGFP  LLKGDAPEEE  VSLSKTVMKF  WANFARSGNP  NGEGLPHWPM

YDQEEGYLQI  GVNTQAAKRL  KGEEVAFWND  LLSKEAAKKP  PKIK
```

In accordance with the present invention, a functional mutant form means a porcine liver esterase subunit which can assemble into enzymically active recombinant porcine liver esterases. This includes those subunits which can be derived from the naturally occurring monomers of porcine liver esterases of types $\alpha$, $\beta$, $\gamma$. Preferably included are artificially generated mutant forms which have been altered around the active site of the resulting enzyme. As a result, enzymic activity and selectivity of the recombinant porcine liver esterase can be increased with respect to a particular substrate.

The term porcine liver esterase subunit further includes those derivatives of the original translation product, which are produced therefrom by post-translational modification.

The individual monomeric subunits of the recombinant porcine liver esterase can form multimers in solution to give a particularly functional enzyme. In this connection, it is also possible for subunits of a different type to be contacted with one another. Moreover, the monomers themselves have enzymic activity which is, however, normally weaker than that of the multimers.

The porcine liver esterases obtained in this way are distinguished by high purity. It is in particular possible to avoid the usual isoenzyme and other hydrolase contaminations occurring in porcine liver esterase extracts. Furthermore, the recombinant porcine liver esterases have increased, sometimes even greatly increased, enantioselectivity, making the use thereof in organic-enzymic syntheses an interesting prospect. It is also particularly interesting that the recombinant porcine liver esterases sometimes show a reversed stereo preference compared to that of commercially available porcine liver esterases. Moreover, the recombinant porcine liver esterases can be produced in a constant quality.

The present invention further relates to nucleic acids coding for the inventive recombinant porcine liver esterase subunits or to DNA fragments which are complementary to such nucleic acid sequences and hybridize with said coding nucleic acids under stringent conditions. For this purpose, it is possible to use common hybridization conditions (e.g. 60° C., 0.1×SSC, 0.1% SDS).

In another preferred embodiment, a stop codon is introduced at the 3' end of the coding region for specific translation termination.

The coding DNA sequences may be cloned into conventional vectors and, after transfection of host cells with such vectors, be expressed in cell cultures. An example of a suitable vector is the vector pUC19 or the vector pCYTEX for transformation of *E. coli* or the vector pPICZα for transformation of the yeast *Pichia pastoris*. Further interesting unicellular organisms which have proved to be suitable as hosts for biotechnological expression of recombinant enzymes are members of the species *Aspergillus* sp., *Schwanniomyces* sp., *Kluyveromyces* sp., *Yarrowia* sp., *Arxula* sp., *Saccharomyces* sp., *Hansenula* sp. or *Pichia* sp. Preferred host organisms which may be mentioned are, apart from *P. pastoris*, *Saccharomyces cerevisiae*, *Aspergillus orycae*, *Schwanniomyces occidentalis*, *Kluyveromyces lactis*, *Yarrowia lipolytica*, *Arxula adeninivrans*, *Pichia methanolica*, *Pichia guilliermondii* or *Hansenula polymorpha*.

In said vectors, the coding DNA fragments must be in the same open reading frame as the promoter. Preferred promoters are especially strong promoters such as, for example, the lac, lambda, T7, T4 promoters, rhamnose inducible promoter and alcohol oxidase (AOXI) promoter. The vectors may contain further functional regions. Apart from selection markers and replication origins, gene-regulatory elements such as, for example, operators, repressors and transcription factors are especially interesting. In particular, vector constructs which permit reversible, inducible or repressable expression of the recombinant porcine liver esterase subunits or of the functional enzyme itself may be used.

Preferred host cells for transfection with vectors containing the inventive coding DNA fragments for expressing porcine liver esterase subunits are unicellular prokaryotic or eukaryotic organisms such as, for example, *Aspergillus* sp., *S. cerevisiae*, *Hansenula* sp., *E. coli* or *P. pastoris*.

Thus, the present invention further relates to the use of DNA fragments coding for a porcine liver esterase subunit of the invention and, where appropriate, for further N- and/or C-terminal domains fused thereto for cloning in vectors, to the use of said vectors for transformation of cells and to the use of such transformed cells or cell cultures for expressing the recombinant porcine liver esterase subunits. The expressed subunits may be isolated, for example, as monomers, but may also form multimers in the medium to give enzymically active recombinant porcine liver esterases, with subsequent isolation of the functional enzyme.

Preference is given to culturing the host cells and to secretorily expressing the porcine liver esterase subunits in liquid-culture containers in a steady-state process.

The activity of the expressed esterase can be checked spectrophotometrically via conversion of selected substrates. The esterase-catalyzed chromophoric cleavage of acetates such as, for example, p-nitrophenyl acetate, has proved suitable for this.

In addition to biotechnological expression of enzymically active recombinant porcine liver esterases, the DNA fragments, expression vectors or expression systems may also be used for mutagenesis. The mutant porcine liver esterases and monomeric subunits thereof, which can then be expressed, may be assayed and selected for their enzymic activity. Several repeats of the mutagenesis, expression and selection cycles make it possible to generate tailor-made enzymic catalysts for organic synthesis. The selection step may be carried out by adding the expressed recombinant enzymes to a reaction mixture containing a potential substrate, and the conversion can be determined spectrophotometrically, for example.

Suitable substrates for catalytic conversion by means of recombinant porcine liver esterase are especially aromatic-aliphatic esters and aliphatic-aliphatic esters, here especially carboxylic esters of chiral or prochiral alcohols, and the carboxylic acid component comprises preferably from 2 to 6, particularly preferably from 2 to 4, carbon atoms and may also be branched.

The enzymically catalytic resolution of the racemates of carboxylic esters, in particular acetates, takes place with high to excellent enantioselectivity. The optimal enzyme activity of recombinant porcine liver esterase containing monomeric subunits according to Seq. Id. No. 1 is at a pH of between 5 and 10, preferably between 7 and 9, and at a temperature of between 20° C. and 90° C., preferably between 30° C. and 80° C., particularly preferably between 40 or 50° C. and 60 or 70° C.

It is furthermore possible to use the recombinant enzymes of the invention also in resolution of the racemates of carboxylic acids or in the conversion of prostereogenic compounds, in particular of diols or dicarboxylic acids.

The invention is illustrated by some exemplary embodiments given below, which, however, should not be regarded as being limiting.

General remarks: microorganisms, media, vectors and oligonucleotides used

The *E. coli* strain DH5α(F⁻ endA1 hsdR17(rk⁻, mk⁺) supE44 rhi-I λ gyrA96 relAI Δ(argF-laczya)U169) is utilized for obtaining and propagating the plasmids used below. The *E. coli* strain DH5α is cultured in $LB_{lowsalt}$ (10 g l⁻¹ yeast extract, 1010 g l⁻¹ peptone and 5 g l⁻¹ NaCl). The culture solution is admixed with 50 mg l⁻¹ nalidixic acid and, where appropriate, with 100 mg l⁻¹ ampicillin or 25 mg l⁻¹ Zeocin (Invitrogen, Carlsbad, Calif., USA).

The yeast *Pichia pastoris* X33 (Invitrogen) was utilized for the expression experiments. The Pichia cells were cultured using the following media:

YPD medium (1% yeast extract, 2% peptone and 2% glucose);

YPDS medium (YPD medium in 1 M sorbitol);

BMGY medium (1% yeast extract, 2% peptone, 100 mM potassium phosphate pH 6, 1.34% yeast nitrogen base with ammonium sulfate and without amino acids, and 1% glycerol);

BMMY medium (BMGY medium, with 0,5% sterile-filtered methanol being used instead of 1% glycerol)

The media are admixed with 100 mg l⁻¹ Zeocin. Media for plates are supplemented with 1.5% agar.

The *E. coli-P. pastoris* vector pPICZαA (Invitrogen) was used in order to clone a DNA sequence coding for a porcine liver carboxyl esterase which is under the control of the alcohol oxidase promoter AOXI.

The oligonucleotide primers used for the PCR are listed in table 1.

TABLE 1

| Oligonucleotide | Nucleotide sequence | | Notes |
|---|---|---|---|
| PLE-1F | 5'-GAT ATC CCG GGC ATA TGT GGC TTC TCC CGC TGG T-3' | (Seq. Id. No. 2) | EcoRV, SmaI NdeI |
| PLE-2R | 5'-GCA TCC GGG AAT TCT CAG CTC AGC ATG CTT TA-3' | (Seq. Id. No. 3) | SmaI, EcoRI |
| PLE-3F | 5'-GGG CAG CCA GCC TCG CCG CCT GTT GTG GAC A-3' | (Seq. Id. No. 4) | — |
| PLE-4R | 5'-TCA CAG CTC AGC ATG CTT TAT CTT GGG TGG C-3' | (Seq. Id. No. 5) | — |
| PLE-5F | 5'-AGC CTG CGC TAC GGT AGC GAA AC-3' | (Seq. Id. No. 6) | — |
| PLE-6R | 5'-TGA AGG GAT CCT AAG TAA GTA G-3' | (Seq. Id. No. 7) | — |
| PLE-7F | 5'-AAG CTG AAT TCG GGC AGC CAG CCT CGC CGC CT-3' | (Seq. Id. No. 8) | EcoRI |
| PLE-8R | 5'-GTC AGT CTA GAT CAC AGC TCA GCA TGC TTT ATC-3' | (Seq. Id. No. 9) | XbaI |
| PLE-9F | 5'-AAG CTG AAT TCG GGC AGC CAG CCT CGC CGC CTG-3' | (Seq. Id. No. 10) | EcoRI |

TABLE 1-continued

| Oligonucleotide | Nucleotide sequence | Notes |
|---|---|---|
| PLE-10R | 5'-ACC TCT AGA TAC TTT ATC TTG GGT GGC TTC-3' | (Seq. Id. No. 11) XbaI |
| PLE-11R | 5'-ACC TCT AGA TCA CTT TAT CTT GGG TGG CTT C-3' | (Seq. Id. No. 12) XbaI |

General remarks: DNA recombination and transformation

Unless stated otherwise, standard methods according to Sambrook, J., Fritsch, E., Maniatis, T. (1989) Molecular Cloning: A Laboratory Manual, 2nd Edn., Cold Spring Habour, N.Y. are used.

Plasmid and DNA extractions are carried out using a QIAprep spin miniprep kit, a plasmid midi kit or a QIAquick gel extraction kit (Qiagen, Hilden, Germany). The restriction enzymes employed are used according to the particular manufacturer's instructions. DNA sequencing is carried out on the basis of both strands with the aid of the Taq Ready Reaction Dye Deoxy™ terminator cycle sequencing kit (Applied Biosystems, Weiterstadt, Germany). The sequencing products are analyzed using a 373 DNA sequencer from the same company.

Competent E. coli cells are prepared and transformed using a standard protocol according to Chung, C. T., Niemela, S. L. & Miller, R. H. (1989) Proc. Natl. Acad. Sci. USA. 86, 2172–2175. P. pastoris is transformed with the relevant plasmids via electroporation.

EXAMPLE 1

Tissue Preparation, mRNA Isolation, and Cloning of cDNA 0.8 g of fresh pig liver tissue is homogenized and the polyA-mRNA released is isolated using the Fast Track 2.0 kit (Invitrogen) according to the manufacturer's instructions. cDNA was synthesized from the mRNA extract by RT-PCR with the aid of the cDNA Cycle™ kit (Invitrogen) according to the kit's protocol, using oligo-dT primers. The RT-PCR products were then used as templates for amplification of porcine liver esterase (PLE). The gene-specific primers used were oligonucleotides PLE-1F (Seq. Id. No. 2) and PLE-2R (Seq. Id. No. 3) (Table 1), which at the same time introduced restriction cleavage sites required for cloning the PCR product. Both primers were prepared on the basis of the sequence of the mRNA of porcine liver proline-α-naphtylamidase (Matsushima, M., et. al. (1991) FEBS Lett. 293, 37–41) which was assumed to have a sequence complementary to PLE. The PCR was carried out in a thermocycler (Robocycle Gradient 40, Stratagene, La Jolla, Calif., USA). A first denaturation step of 5 minutes at 95° C. was followed by 28 cycles according to the following temperature program: 1 min at 95° C., 2 min at 55° C. and –3 min at 72° C.

The purified PCR product is cloned via its blunt ends into the SmaI restriction cleavage site of vector pUC19. The resulting vector, pUC19-PLE-R, was used for transformation of E. coli DH5α strains and the plasmid was propagated by culturing the transformed strains. The plasmid was isolated from the recombinant E. coli strains, identified by determining its size or via restriction mapping and used as template for PCR amplification of the PLE sequence. The amplified PLE sequence was then sequenced.

EXAMPLE 2

Construction of an Expression Vector for E. coli and P. pastoris:

For intracellular expression of the cloned PLE in E. coli, the vector pUC19-PLE-R was cut with NdeI and EcoRI, resulting in a 1705 bp fragment coding for the complete naturally occurring PLE sequence. The restriction fragment obtained is inserted into the NdeI/EcoRI restriction cleavage site of pT1-BTL2 (Belev, T. N. et. al. (1991) Plasmid, 26,147–150), forming a new vector, pCYTEX-PLE (6652 bp).

For periplasmic expression of PLE sequences without the N-terminal leader sequence (mPLE), the corresponding DNA sequence was amplified using primers PLE-3F (Seq. Id. No. 4) and PLE-4R (Seq. Id. No. 5) (table 1) and ligated via its blunt end into the pT1-ompA sequence of the vector pT1-ompA-BTL2 (Rua, M. L., et. al. Appl. Microbiol. Biotechnol. 49, 405–410) which can likewise be amplified with the aid of primers PLE-5F (Seq. Id. No. 6) and PLE-6R (Seq. Id. No. 7) (table 1). The resulting vector (which no longer contains the BTL2 gene) is denoted pCYTEX-ompA-mPLE (6682 bp) and contains the mPLE gene in the open reading frame of the ompA leader sequence under the control of a heat-inducible λ promoter. For expression of the mPLE gene in P. pastoris, the mPLE DNA sequence was cloned into the open reading frame behind an α factor-signal sequence of the E. coli-P. pastoris vector pPICZαA (from Invitrogen). The mPLE gene was then amplified using primers PLE-7F (Seq. Id. No. 8) and PLE-8R (Seq. Id. No. 9) (table 1), and the amplification product is cut using the restriction enzymes NdeI and XbaI and ligated into the corresponding restriction cleavage site of vector pPICZαA. The resulting vector is denoted pPICZα-mPLE.

Furthermore, expression vectors were constructed, in whose expression product the HAEL tetrapeptide at the C-terminal end has been deleted. For this purpose, the mPLE gene was amplified by means of primers PLE-9F (Seq. Id. No. 10) and PLE-10R (Seq. Id. No. 11) or PLE-11 R (Seq. Id. No. 12). Both PCR products were ligated into the EcoRI/XbaI restriction cleavage site of pPICZαA. The fragments, generated with the aid of primer PLE-10R, result in a fusion protein containing myc und His tag domains which are already encoded on the original pPICZαA vector. The PCR product obtainable by using primer PLE-11 contains no C-terminal tags, since the primer introduces a stop codon which prevents fusion with the tag domains of vector pPICZαA.

All resulting vectors, pPICZα-mPLE (5183 bp), pPICZα-mPLE*-1 (5170 bp) and pPICZα-mPLE*-2 (5171 bp), are linearized at the PmeI restriction cleavage site and introduced into *P. pastoris* by means of electroporation (Invitrogen).

FIG. 1 depicts the prepared vectors diagrammatically.

EXAMPLE 3

Expression of Recombinant PLE in *E. coli* DH5α

Recombinant *E. coli* DH5α clones which have been transformed with vector pCYTEX-PLE or pCYTEX-ompA-mPLE are cultured in LB medium at 37° C., 200 rpm to a cell density of $OD_{578}$ 0.8 to 1.0. Expression of the recombinant protein was induced by increasing the temperature to 42° C. Every hour, a sample was removed, and the cells were harvested 3 to 4 hours after induction and stored at −20° C. or analyzed directly by means of SDS-PAGE or an activity assay.

EXAMPLE 4

Culturing and Secretory Expression of Recombinant PLE in *P. pastoris*

Recombinant clones selected on Zeocin-containing culture medium were picked and cultured in YPDS medium at 30° C., 200 rpm to a cell density of $OD_{600}$ approx. 15. 25 ml of a BMGY medium were inoculated with 200 μl of said culture and cultured overnight at 30° C. The yeast cells were then isolated by centrifugation at 3000 g and 4° C. for five minutes and transferred to BMMY induction medium, the culture growing to a cell density of $OD_{600}$ 1.0. Induction is carried out by daily addition of 0.5% (v/v) methanol. After inducing for 96 hours, the cells were harvested by centrifugation. The supernatants contain the recombinant enzyme which is concentrated by centrifugation at 4000 g and 4° C. for 15 minutes with the aid of 20-ml Centricon tubes (NMWL 30000, Ultracel-PL membrane, Millipore). The activity of the culture during the growth phase and of the concentrated enzyme-containing medium was determined using a pNPA assay and the proteins were identified with the aid of gel electrophoresis (a more detailed description follows.). The reference used for densitometric determination of the protein concentration was serum albumin of known concentrations.

EXAMPLE 5

SDS Polyacrylamide Gel Electrophoresis

10 μl of 2×SDS sample buffer were added to 20 μl of commercially available porcine liver esterase (100 U, according to pNPA assay) dissolved in 2 ml or 20 μl of the 10-fold concentrated *P. pastoris*-culture supernatant. After heating the solution to 95° C. for 5 min, the proteins are separated on a 12.5% strength polyacrylamide gel, 4% strength stacking gel. The protein is detected by staining the samples with Coomassie Brilliant Blue R250. To determine esterase activity, the proteins were renatured for 12 hours in a Triton X-100 solution (0.5% in 0.1 M Tris/HCl pH 7.5). A 1:1 mixture of solution A (20 mg of α-naphthylacetate dissolved in 5 ml of acetone and subsequent addition of 50 ml of 0.1 M Tris/HCl pH 7.5, 50 mg of Fast Red TR salt dissolved in 50 ml of 0.1 M Tris/HCl, pH 7.5) and solution B (50 mg of Fast Red TR salt dissolved in 50 ml of 0.1 M Tris/HCl, pH7.5) was then added to the gel. A red α-naphthyl form of Fast Red is formed in the presence of hydrolytic lipase or esterase activity (Krebsfänger, N., et al., (1998) Enzyme Microb. Technol. 22, 641–646).

EXAMPLE 6

N-Terminal Protein Sequencing

The commercially available PLE fraction is separated and blotted from an SDS-PAGE gel to a PVDF membrane (Matsudaira, P. (1987) J. Biol. Chem. 262,10035–10038). Sequencing is carried out using a gas phase sequencer.

EXAMPLE 7

Determination of Esterase Activity

The esterase activity is determined spectrophotometrically in a sodium phosphate buffer (50 mM, pH 7.5). p-Nitrophenylacetate (10 mM dissolved in DMSO) is used as a substrate. The amount of p-nitrophenol liberated is measured at 410 nm ($\epsilon=12.36\times10^3 M^{-1}cm^{-1}$) at room temperature. Additionally, the enzyme activity was determined for different pH values. The unit U defines an esterase activity which converts 1 μmol of p-nitrophenol per minute under assay conditions. PLE substrate specificity was determined using a pH-stat assay. For this purpose, a defined amount of esterase is added at a temperature of 37° C. to 30 ml of an emulsion containing 5% (v/v) of an ester (methyl butyrate, ethyl caprylate, ethyl acetate, triolein, tricaprylin) and 2% (w/v) gum arabic. The acid liberated is titrated automatically with 0.01 N NaOH with the aid of a pH-stat device (Schott, Mainz, Germany), in order to maintain a constant pH of 7.5. One U corresponds to a consumption of 1 μmol of acid per minute under assay conditions. The activity was determined at different temperatures at pH 7.5 using ethyl caprylate as substrate. The highest activity determined was defined as 100%.

EXAMPLE 8

Determination of Proline-β-Naphthylamidase Activity

The proline-β-naphthylamidase activity is determined spectrophotometrically using proline-β-naphthylamide (0.2 mM in DMSO) as substrate. The reaction is carried out in a mixture containing 0.1 M Tris/HCl buffer pH 8.0 and 50 μl of substrate, to which 0.4 U (according to pNPA assay) of recombinant or commercially available PLE preparations is added at 37° C. for 30 min. The reaction is stopped by adding 1.5 ml of coupling reagent FastGarnet (Sigma) (Barret, A. J., (1977) Proteinases in Mammalian Cells and Tissues Barret, A. J., ed pp. 181–208, Elsevier, Amsterdam). The amount of β-naphthylamine liberated is determined at 520 nm ($\epsilon=24.03\times10^3 M^{-1}cm^{-1}$). One U of amidase activity is defined as the amount of enzyme which liberates 1 μmol of β-naphthylamine per minute under assay conditions.

The PLE expression products of the vectors pCYTEX-PLE, containing the PLE gene with the native leader sequence, and pCYTEX-PLE-ompA-mPLE, containing the mPLE nucleic acid sequence fused to the ompA leader sequence which should ensure secretion of the esterase enzyme into the periplasmic space (FIGS. 1, 2) and 3) (Beer, H. D., et. al., Biochim. Biophys. Acta. 1399,173–180) depict the vector constructs diagrammatically). However, none of the transfected cultures was able to express enzymically active, native or recombinant porcine liver esterase; both the SDS PAGE and esterase activity assays were negative.

Vectors according to the diagrammatic representation in FIG.. 1, 4) to 6) are used for expressing recombinant porcine liver esterase in *P. pastoris*. The vector depicted in FIG. 1, 5) (pPICZα-mPLE*-1) contains, in addition to the N-terminal secretion signal Alpha (.alpha. factor), the C-terminal tags myc and His(6X) which both originate from vector pPICZαA. The construct 6) (ρPICZa-mPLE*2), depicted in FIG. 1, contains no C-terminal tags, since here a stop codon was introduced into the reading frame in front of the corresponding vector regions. The vector constructs lack the C-terminus HAEL which is present in native porcine liver esterase at the C-terminus. The third *P. pastoris* vector prepared (pPICZα-mPLE, FIG. 1, 4)) still has the C-terminal natural tetrapeptide sequence HAEL (ER). The vectors were linearized and used for transfecting *P. pastoris*. The supematants of 30 clones were in each case tested for active expression of the cloned enzyme with the aid of the pNPA assay. In the case of vector FIG. 1, 4), no esterase activity was found. In contrast, it was shown that, by using vectors according to FIG. 1, 5) or 6) which lack the coding region for the native C terminus, it was possible to actively express and secrete. In each case, one clone with and one without C-terminal tag were picked and further characterized.

The activity of the supernatants used for further studies was determined to 0.5 U/ml with the aid of the pNPA assay, after culturing the picked clones for 96 hours. After concentrating the enzymes by centrifugation, an activity of 10 U/ml was obtained, corresponding to a specific protein activity of approx. 500 U/mg. The fraction $V_{max}/K_m$ of the recombinant porcine liver esterase of the invention is 139 $min^{-1}mg^{-1}$ for the substrate pNPA (values compared to a commercially available porcine liver esterase extract are listed in table 2 below).

TABLE 2

| Esterase | $V_{max}$ (U/mg$^{-1}$) | $K_m$ (mM) | $V_{max}/K_m$ (min$^{-1}$mg$^{-1}$) |
| --- | --- | --- | --- |
| recombinant PLE | $0.74 \times 10^3$ | 5.32 | 139 |
| PLE commercial extract (Fluka) | $1.58 \times 10^3$ | 1.82 | 868 |

The recombinant PLE of the invention cleaves ethyl caprylate and tributyrin with an activity of about 50 U/mg and ethyl acetate with an activity of about 20 U/mg. Triolein is not cleaved, as is expected for a pure esterase. The commercial extracts (Fluka or Roche (Chirazyme E-2)), on the other hand, hydrolyze triolein, indicating contaminations by lipases or PLE isoenzymes.

Figure 2:
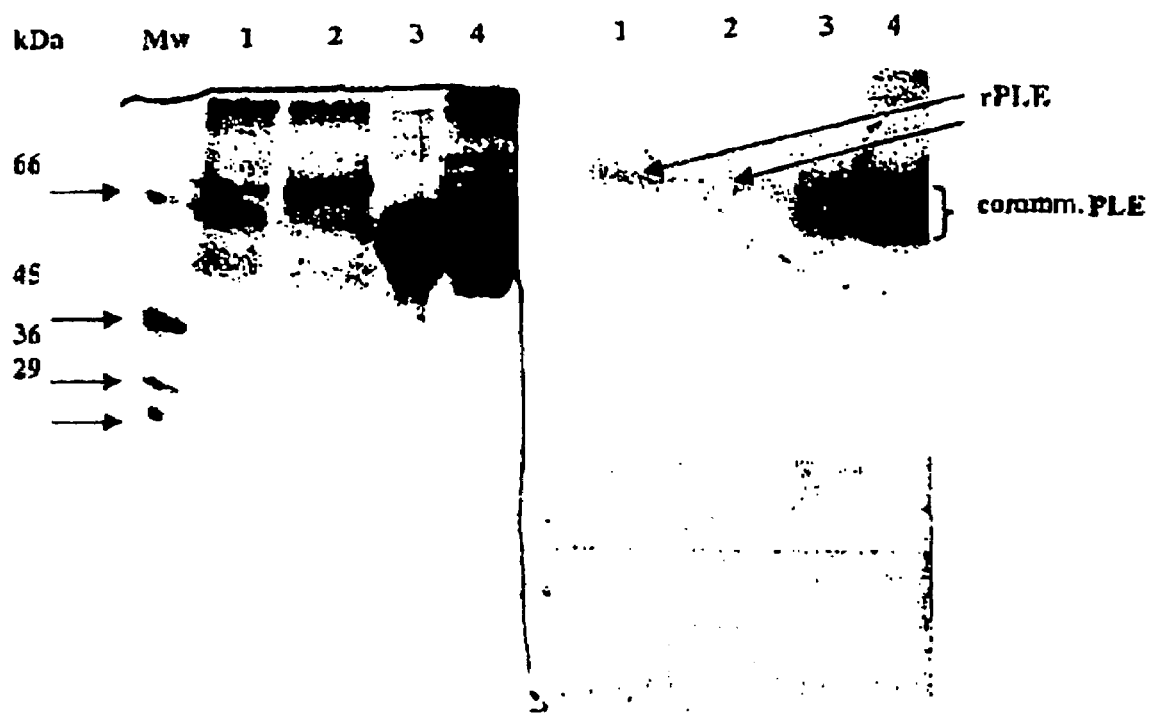
FIG. 2 depicts SDS-PAGE analysis (left) and activity detection (right). The molecular weight of the inventive recombinant subunit of porcine liver esterase (Seq. Id. No. 1 with C-terminal tags, lanes 1 and 2, 4 U of PLE-Fluka, lane 3, 4 U of PLE-Chirazyme-E2, lane 4; Mw=molecular weight standard).

FIG. 2 depicts SDS-PAGE analysis (left) and activity detection (right). The molecular weight of the inventive recombinant subunit of porcine liver esterase (Seq. Id. No. 1 with C-terminal tags, lanes 1 and 2 in FIG. 2, Mw=molecular weight standard) is approx. 61 to 62 kDa, as determined by SDS-PAGE analysis. The activity analysis using Fast Red shows a sharp band of the recombinant porcine liver esterase of the invention (0.4 U), whereas the commercial extracts give a smear, and this can be attributed to the presence of different isoenzymes or other hydrolases (4 U of PLE-Fluka, lane 3, 4 U of PLE-Chirazyme-E2, lane 4, FIG. 2).

Measurement of the enzymic activity at different temperatures and pH shows an optimum at 60° C. (pH 7.5) with respect to ethyl caprylate hydrolysis, and the esterase of the invention is completely inactivated at 70° C. and has an optimum at approx. pH 8 (37° C.).

Figure 3:
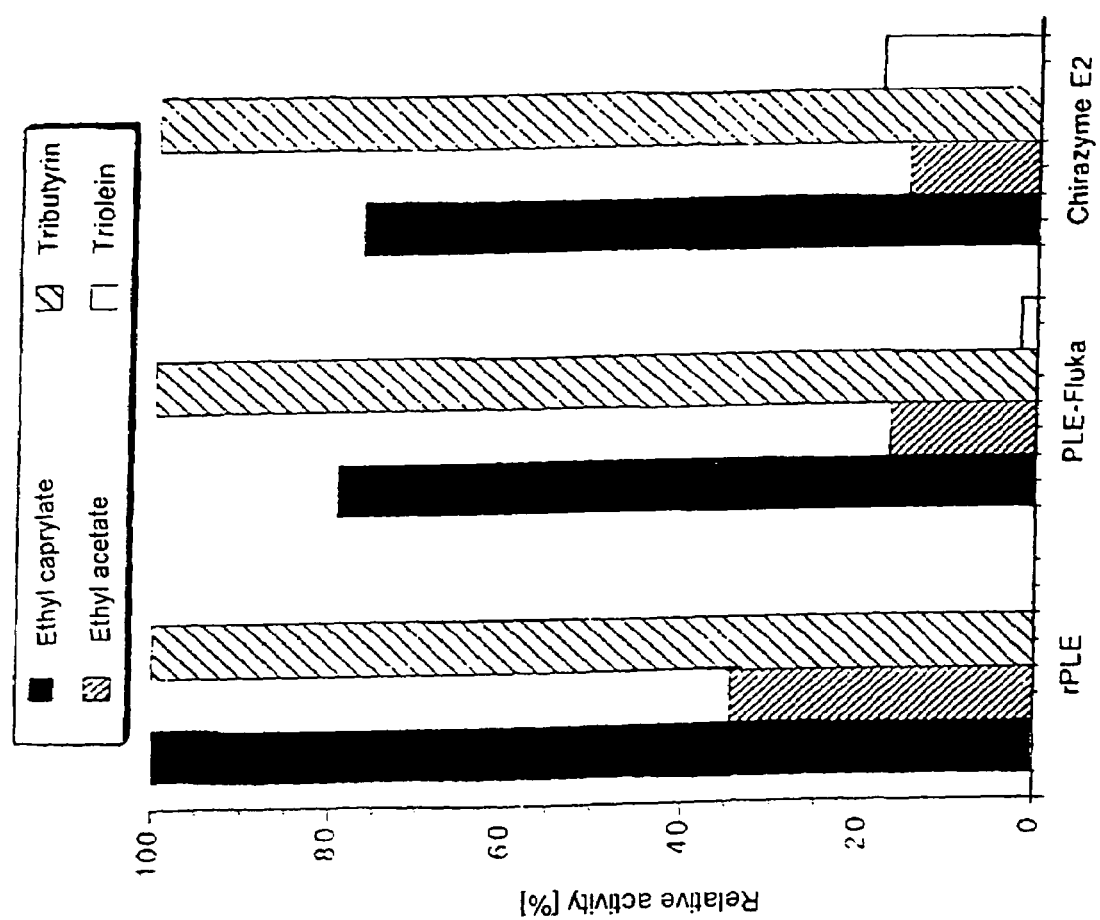
FIG. 3 depicts the relative activities of the recombinant PLE (rPLE) of the invention and of the commercial PLE extracts (PLE-Fluka, Chirazyme E2) with respect to the substrates ethyl caprylate, ethyl acetate, tributyrin and triolein.

FIG. 3 depicts the relative activities of the recombinant PLE (rPLE) of the invention and of the commercial PLE extracts (PLE-Fluka, Chirazyme E2) with respect to the substrates ethyl caprylate, ethyl acetate, tributyrin and triolein.

Figure 4:
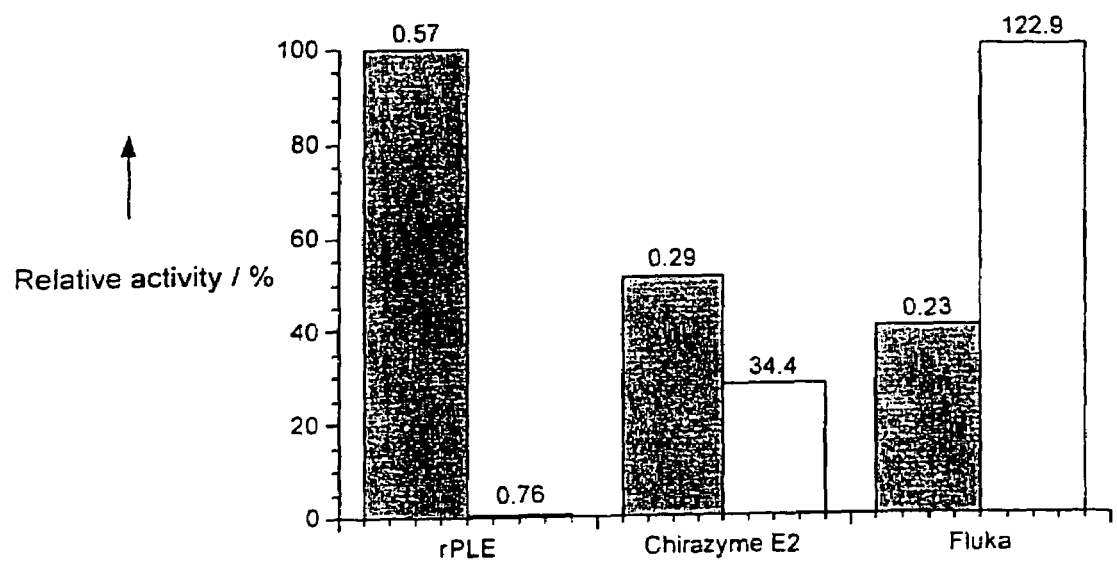
FIG. 4 depicts the relative activities of the enzymes for the substrates proline-$\beta$-naphthylamide (PNA, black bar) and methyl butyrate (white bar).

FIG. 4 depicts the relative activities of the enzymes for the substrates proline-β-naphthylamide (PNA, black bar) and methyl butyrate (white bar).

EXAMPLE 9

Further Characterization of the Recombinant Porcine Liver Esterase Obtained

Native Polyacrylamide Gel Electrophoresis

10 μl of commercially available PLE (0.1 U) and 5–10 μl of the concentrated *P. pastoris* culture supernatants were mixed with 10 μof a sample buffer. The samples were separated on a 7.5% polyacrylamide gel with 4% stacking gel. The gels were activity stained and then stained with Coomassie Brilliant Blue.

Figure 5:
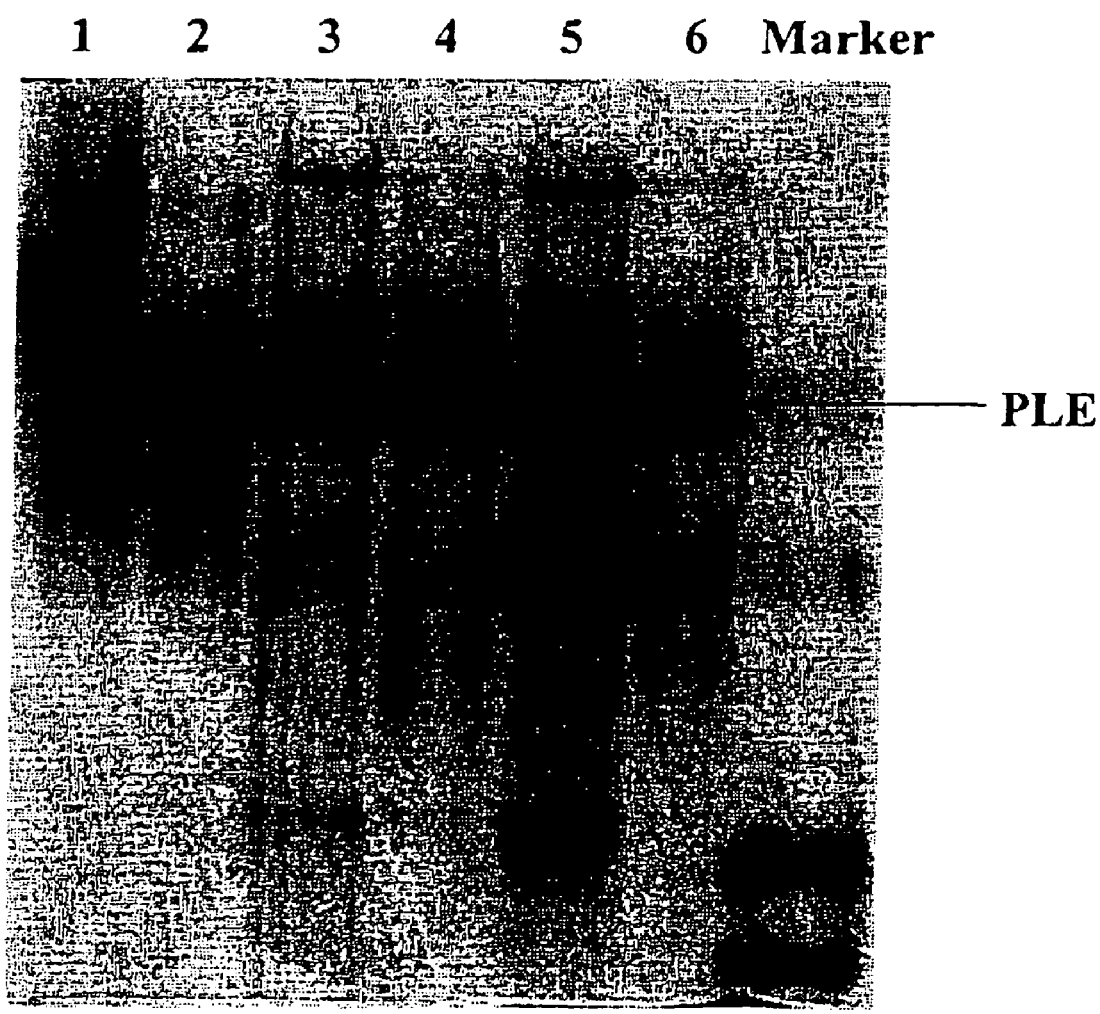
FIG. 5 depicts the results of native PAGE of recombinant and commercial PLEs. Mw: molecular weight standards (272 kDa, jack bean urease (trimer); 132 kDa (dimer) and 66 kDa (monomer), bovine serum albumin; 45 kDa, chicken egg albumin); lane 1:0.1 U of Fluka PLE; lane 2: 0.07 U of Chirazyme E-2; lanes 3–6: 0.1, 0.045, 0.09 and 0.045 U of rPLE (samples from various cultures), units based on a PNPA test.

FIG. 5 depicts the results of native PAGE of recombinant and commercial PLEs. Mw: molecular weight standards (272 kDa, jack bean urease (trimer); 132 kDa (dimer) and 66 kDa (monomer), bovine serum albumin; 45 kDa, chicken egg albumin); lane 1:0.1 U of Fluka PLE; lane 2: 0.07 U of Chirazyme E-2; lanes 3–6: 0.1, 0.045, 0.09 and 0.045 U of rPLE (samples from various cultures), units based on a pNPA test.

Isoelectric Focusing

1–5 μl of concentrated *P. pastoris* culture supernatants (0.02–0.1 U) were mixed with 10 μl of a sample buffer. The samples were separated on a 5% polyacrylamide gel containing carrier ampholyte (2.4%; pH 3–10; Serva). The gels were activity-stained, fixed with trichloroacetic acid solution (10% (w/v) for 10 min, then 1% (w/v) overnight) and subsequently stained with Coomassie Brilliant Blue. The isoelectric point of the recombinant PLE is pl: 4.78

EXAMPLE 10

Esterase-Catalyzed Resolution of Acetate Racemates

For esteraser-catelyzed hydrolysis, 10 mmol of an acetate were dissolved in sodium phosphate buffer (pH 7.5, 50 mmol) and introduced into 1 ml reaction vessels, and resolution of racemates was started by adding 0.5 unit (based on the pNPA assay) of esterase. The reaction was stopped by extracting the mixture with methylene chloride and drying the organic phase over anhydrous sodium sulfate. Enantiomeric purity and conversion were determined by gas chromatography (column: heptakis(2,6-O-methyl-3-O-pentyl)-β-cyclodextrin, carrier gas: $H_2$, flame ionization detector).

The following acetate substrates were enzymically converted:

1-Phenyl-1-ethyl acetate 1,1-phenyl-2-propyl acetate 2,1-phenyl-2-butyl acetate 3, 1-phenyl-1-propyl acetate 4,1-phenyl-3-propyl acetate 5,1-phenyl-2-pentyl acetate 6

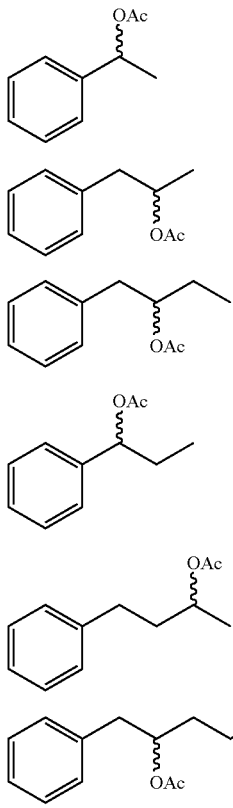

The products (alcohols) of kinetic resolution of racemates by porcine liver esterase are denoted 1a–6a accordingly.

Retention times: 1 (100° C. isothermal): (S)-1 3.7 min; (R)-1, 5.8 min; (R)-1a 6.7 min; (S)-1a, 7.6 min; 2 (75° C. isothermal): (S)-2 26.5 min; (R)-2, 42.3 min; (S)-2a 32.6 min; (R)-2a, 34.2 min. 3 (90° C. isothermal): (S)-3 17.6 min; (R)-3, 20.2 min; (S)-3a 24.8 min; (R)-3a, 27.4 min. 4 (80° C. isothermal): (S)-4 13.9 min; (R)-4 20.9 min; (S)-4a 51.5 min; (R)-4a 44.6 min. 5 (100° C. isothermal): (S)-5 15.6 min; (R)-5 28.7 min; (S)-5a 19.1 min; (R)-5a, 20.5 min. 6 (90° C./30'/5° C./min//110° C.): (S)-6: 29.1 min and (R)-6 30.4 min; (S)-6a 37.3 min and (R)-6a 38.3 min.

Determination of Absolute Configuration:

The absolute configuration of 1 was based on comparison with commercial (R)-1. In the case of 2, 3 and 4, the (R) preference of the lipase Amano PS, which is known from the literature, was referred to (Gutman, A. L., et al., Tetrahedron: Assymmetry (1993) 4, 839–844).

The absolute configuration of 5 was based on the preference of the commercial lipase: lipase Amano AK, R preference, which is known from the literature (K. Burgess, L D Jenning, J. Am. Chem. Soc 1991,113, 6129) for 1-phenyl-3-butanol (5a)

The absolute configuration of 6 is based on measuring the rotation of the optically pure alcohol and comparing it with literature data (U. P. Dhokte, P. M. Pathare, V. K. Mahindroo, H. C. Brown, J. Org. Chem. 1998, 63, 8276–8283).

The enantioselectivity E can be calculated according to Chen, C. S. et al., J. Am. Chem. Soc. 104 (1982), 7294.

The results are summarized in tables 3 to 8.

TABLE 3

Enantioselectivity of various porcine liver esterases in the kinetic resolution of the racemates of (R,S)-1-phenyl-1-ethyl acetate 1

| PLE source[a] | Time (h) | Enantiomeric excess | | Conversion (%) | E[b] |
|---|---|---|---|---|---|
| | | (% ee$_S$) | (% ee$_R$) | | |
| Recombinant | 1 | 58 (S) | 53 (R) | 53 | 5.7 |
| Fluka | 1.5 | 65 (S) | 56 (R) | 54 | 6.8 |
| Sigma | 1 | 72 (S) | 58 (R) | 55 | 7.8 |
| Chirazyme E-1 | 5 | 73 (S) | 58 (R) | 56 | 7.9 |
| Chirazyme E-2 | 1 | 61 (S) | 56 (R) | 52 | 6.5 |

[a]In all reactions, 0.5 unit (based on pNPA assay) was used.
[b]Enantioselectivity E was calculated according to Chen et al. (1982).

TABLE 4

Enantioselectivity of various porcine liver esterases in the kinetic resolution of the racemates of (R,S)-1-phenyl-2-propyl acetate 2

| PLE source[a] | Time (h) | Enantiomeric excess | | Conversion (%) | E[b] |
|---|---|---|---|---|---|
| | | (% ee$_S$) | (% ee$_R$) | | |
| Recombinant | 2 | 75 (R) | 70 (S) | 52 | 12.6 |
| Fluka | 1.5 | 35 (S) | 44 (R) | 44 | 3.6 |
| Sigma | 1.5 | 24 (S) | 32 (R) | 43 | 2.4 |
| Chirazyme E-1 | 1.5 | 22 (S) | 43 (R) | 34 | 3.1 |
| Chirazyme E-2 | 1 | 9 (S) | 9 (R) | 50 | 1.3 |

[a],[b]see table 3

TABLE 5

Enantioselectivity of various porcine liver esterases in the kinetic resolution of the racemates of (R,S)-1-phenyl-2-butyl acetate 3

| PLE source[a] | Time (h) | Enantiomeric excess | | Conversion (%) | E[b] |
|---|---|---|---|---|---|
| | | (% ee$_S$) | (% ee$_R$) | | |
| Recombinant | 2 | 57 (R) | >99 (S) | 36 | >>100 |
| Fluka | 2 | 12 (R) | 12 (S) | 49 | 1.4 |
| Sigma | 1 | 17 (R) | 11 (S) | 59 | 1.5 |
| Chirazyme E-1 | 2 | 19 (R) | 18 (S) | 52 | 1.7 |
| Chirazyme E-2 | 1 | 58 (R) | 40 (S) | 59 | 4 |

[a],[b]see table 3

TABLE 6

Enantioselectivity of various porcine liver esterases in the kinetic resolution of the racemates of (R,S)-1-phenyl-1-propyl acetate 4

| PLE[a] | Time [h] | Enantiomeric excess | | Conversion [%] | E[b] |
|---|---|---|---|---|---|
| | | [% ee$_S$][c] | [% ee$_P$][c] | | |
| Recombinant | 4 | 13 | 20 | 40 | 1.7 |
| Fluka | 1 | 21 | 28 | 43 | 2.2 |
| Sigma | 0.5 | 17 | 19 | 48 | 1.7 |
| Chirazyme E-1 | 0.5 | 9 | 13 | 41 | 1.4 |
| Chirazyme E-2 | 0.5 | 18 | 27 | 40 | 2.1 |

[a],[b]see table 3
[c]In all cases, the product alcohol 4a was in (R) configuration and the unreacted acetate 4 in (S) configuration.

TABLE 7

Enantioselectivity of various porcine liver esterases in the kinetic resolution of the racemates of (R,S)-4-phenyl-2-butyl acetate 5

| PLE[a] | Time [h] | Enantiomeric excess [% ee$_S$] | [% ee$_P$] | Conversion [%] | E[b] |
|---|---|---|---|---|---|
| Recombinant | 2 | 52 (R) | 59 (S) | 47 | 6.3 |
| Fluka | 0.5 | 31 (S) | 42 (R) | 42 | 3.2 |
| Sigma | 0.25 | 22 (S) | 25 (R) | 47 | 2.1 |
| Chirazyme E-1 | 0.5 | 25 (S) | 29 (R) | 47 | 2.3 |
| Chirazyme E-2 | 0.25 | 1 (R) | 2 (S) | 43 | 1.1 |

[a],[b] see table 3

TABLE 8

Enantioselectivity of various porcine liver esterases in the kinetic resolution of the racemates of (R,S)-1-phenyl-2-pentyl acetate 6

| PLE[a] | Time [h] | Enantiomeric excess [% ee$_S$][c] | [% ee$_P$][c] | Conversion [%] | E[b] |
|---|---|---|---|---|---|
| Recombinant | 2 | 69 | 78 | 47 | 16.7 |
| Fluka | 0.3 | 24 | 26 | 48 | 2.1 |
| Sigma | 0.5 | 15 | 13 | 52 | 1.5 |
| Chirazyme E-1 | 0.5 | 9 | 11 | 46 | 1.3 |
| Chirazyme E-2 | 0.3 | 21 | 24 | 46 | 2.0 |

[a],[b] see table 1
[c] In all cases, the product alcohol 6a was in (S) configuration and the unreacted acetate 6 in (R) configuration.

The example shows that the recombinant porcine liver esterase used has a higher enantioselectivity than enzyme extracts. This is particularly evident in the case of phenylalkyl acetates esterified in position 2 or 3.

EXAMPLE 11

Preparation of Enzyme Substrates

The substrates may be synthesized according to chemical standard methods. The synthesis of substrates (2)–(6) and precursor (6a) is described below. All other substrates are commercially available.

40 mmol of acetic chloride are dissolved in 20 ml of pyridine at 4° C. Subsequently, 40 mmol of the alcohol (1-phenyl-2-propanol 2a, 1-phenyl-2-butanol 3a, 1-phenyl-1-propanol 4a, 1-phenyl-3-propanol 5a, 1-phenyl-2-pentanol 6a) are added dropwise with vigorous stirring and mixed at room temperature for 20 h. The reaction mixture is then admixed with diethyl ether and washed twice with saturated sodium bicarbonate solution. The organic phase is dried over anhydrous sodium sulfate and the solvent is removed in a rotary evaporator. The acetate is then isolated by silica gel chromatography (hexane:ethyl acetate 5:1) in a yield of 91% (2), 74% (3), 43% (4) or 87% (5). The acetate (6) was isolated by column chromatography with hexane:ethyl acetate 3:1 in a yield of 25% (6).

Synthesis of (R,S)-1-phenyl-2-pentanol (6a)

100 mmol of phenyl acetaldehyde in 16 ml of absolute diethyl ether are added dropwise and with stirring to the same volume of a Grignard reagent solution of 80 mmol of propylmagnesium chloride in diethyl ether. Following the addition, the reaction mixture is heated with stirring in the water bath for 2 hours and then cooled. Crushed ice is added, followed by admixing semi-concentrated hydrochloric acid in such an amount that the resulting precipitate dissolves. The ether phase is removed and the aqueous phase is then extracted twice more with diethyl ether. The combined extracts are washed with saturated sodium hydrogen sulfite solution, bicarbonate solution and a little water. After drying over anhydrous sodium sulfate, the ether is distilled off and the residue is fractionated by distillation. The product was isolated in a yield of 48%.

The invention claimed is:

1. A recombinant subunit of porcine liver esterase having esterase activity, which comprises SEQ ID NO:1 lacking from 1 to 50 amino acids at the C-terminus.

2. The recombinant subunit of porcine liver esterase of claim 1, lacking from 3 to 10 amino acids at the C-terminus.

3. The recombinant subunit of porcine liver esterase of claim 1, lacking a sequence found in a wildtype porcine liver esterase of histidine, alanine, glutamic acid, and leucine (HAEL) at the C-terminus.

4. A recombinant subunit of porcine liver esterase having esterase activity, which is encoded by a polynucleotide sequence which hybridizes under stringent conditions to a polynucleotide sequence encoding SEQ ID NO: 1, wherein the stringent conditions comprise hybridization at 60° C. in 0.1 ×SSC and 0.1% SDS, and wherein the esterase lacks from 1 to 50 amino acids at the C-terminus.

5. The recombinant subunit of porcine liver esterase of claim 4, which lacks from 3 to 10 amino acids at the C-terminus.

6. The recombinant subunit of porcine liver esterase of claim 4, which lacks a sequence found in a wildtype porcine liver esterase of histidine, alanine, glutamic acid, and leucine (HAEL) at the C-terminus.

7. The recombinant subunit of a porcine liver esterase as claimed in claims 1 or 4, which lacks 1 to 50 amino acids at its N-terminal end.

8. A recombinant protein, comprising the porcine liver esterase as claimed in claims 1 or 4 and a secretion signal domain fused to the N terminus and/or a tag domain is fused to the C terminus.

9. The recombinant protein, as claimed in claim 8, which comprises a secretion signal domain fused to the N-terminus, and which secretion signal domain is encoded by SEQ ID NO:8 or SEQ ID NO:10.

10. The recombinant protein as claimed in claim 9, which comprises a tag domain to the C-terminus and wherein the tag domain is a poly histidine-tag domain and/or a myc-tag domain.

11. The recombinant subunit of porcine liver esterase as claimed in claim 1 or 4, which has been post-translationally modified.

12. An isolated DNA which codes for a porcine liver esterase subunit as claimed in claims 1 or 4.

13. The DNA as claimed in claim 12, which comprises a stop codon at the 3' end of the coding region.

14. A vector comprising the DNA as claimed in claim 12.

15. An enzymatically active recombinant porcine liver esterase comprising a porcine liver esterase subunit as claimed in claims 1 or 4.

16. The enzymatically active recombinant porcine liver esterase as claimed in claim 11, wherein the subunit has been post-translationally modified.

17. An isolated cell transformed with the vector as claimed in claim 14.

18. The cell of claim 17, which is a unicellular prokaryotic cell.

19. The cell of claim 17, which is a eukaryotic cell.

20. The cell of claim 17, which is selected from the group consisting of an *Aspergillus* sp. cell, a *Schwanniomyces* sp. cell, a *Kluyveromyces* sp cell., a *Yarrowia* sp.cell, an *Arxula* sp. cell, a *Saccharomyces* sp. cell, a *Hansenula* sp. cell, a *Pichia* sp.cell and an *E. coli* cell.

21. A method of making a mutated enzymatically active porcine liver esterase comprising:
    mutagenizing the DNA of claim 12;
    expressing the DNA to produce a protein; and
    selecting for an expressed protein that has esterase activity when multimerized.

22. A method for expressing a porcine liver esterase subunit comprising:
    culturing the cell as claimed in claim 17.

23. A method for expressing a porcine liver esterase subunit comprising:
    culturing the cell as claimed in claim 18.

24. A method for expressing a porcine liver esterase subunit comprising:
    culturing the cell as claimed in claim 19.

25. A method of resolving racemates of carboxylic acids, or their ester derivatives, comprising:
    contacting carboxylic acids, or their ester derivatives, with the porcine liver esterase as claimed in claim 11.

26. A method of converting a prostereogenic compound, comprising:
    contacting the prostereogenic compound with the porcine liver esterase as claimed in claim 11.

* * * * *

SEQUENCE LISTING

<160> NUMBER OF SEQ ID NOS: 12

<210> SEQ ID NO 1
<211> LENGTH: 544
<212> TYPE: PRT
<213> ORGANISM: Artificial Sequence
<220> FEATURE:
<223> OTHER INFORMATION: Synthetic Peptide

<400> SEQUENCE: 1

```
Gly Gln Pro Ala Ser Pro Pro Val Val Asp Thr Ala Gln Gly Arg Val
1               5                   10                  15

Leu Gly Lys Tyr Val Ser Leu Glu Gly Leu Ala Gln Pro Val Ala Val
            20                  25                  30

Phe Leu Gly Val Pro Phe Ala Lys Pro Pro Leu Gly Ser Leu Arg Phe
        35                  40                  45

Ala Pro Pro Gln Pro Ala Glu Pro Trp Ser Phe Val Lys Asn Thr Thr
```

-continued

```
                50                  55                  60
Ser Tyr Pro Pro Met Cys Cys Gln Asp Pro Val Glu Gln Met Thr
 65                  70                  75                  80

Ser Asp Leu Phe Thr Asn Gly Lys Glu Arg Leu Thr Leu Glu Phe Ser
                     85                  90                  95

Glu Asp Cys Leu Tyr Leu Asn Ile Tyr Thr Pro Ala Asp Leu Thr Arg
                100                 105                 110

Arg Gly Arg Leu Pro Val Met Val Trp Ile His Gly Gly Leu Val
                115                 120                 125

Leu Gly Gly Ala Pro Met Tyr Asp Gly Val Val Leu Ala Ala His Glu
130                 135                 140

Asn Val Val Val Ala Ile Gln Tyr Arg Leu Gly Ile Trp Gly Phe
145                 150                 155                 160

Phe Ser Thr Gly Asp Glu His Ser Arg Gly Asn Trp Gly His Leu Asp
                165                 170                 175

Gln Val Ala Ala Leu His Trp Val Gln Glu Asn Ile Ala Asn Phe Gly
                180                 185                 190

Gly Asp Pro Gly Ser Val Thr Ile Phe Gly Glu Ser Ala Gly Gly Glu
                195                 200                 205

Ser Val Ser Val Leu Val Leu Ser Pro Leu Ala Lys Asn Leu Phe His
210                 215                 220

Arg Ala Ile Ser Glu Ser Gly Val Ala Leu Thr Val Ala Leu Val Arg
225                 230                 235                 240

Lys Asp Met Lys Ala Ala Lys Gln Ile Ala Val Leu Ala Gly Cys
                245                 250                 255

Lys Thr Thr Thr Ser Ala Val Phe Val His Cys Leu Arg Gln Lys Ser
                260                 265                 270

Glu Asp Glu Leu Leu Asp Leu Thr Leu Lys Met Lys Phe Leu Thr Leu
                275                 280                 285

Asp Phe His Gly Asp Gln Arg Glu Ser His Pro Phe Leu Pro Thr Val
                290                 295                 300

Val Asp Gly Val Leu Leu Pro Lys Met Pro Glu Glu Ile Leu Ala Glu
305                 310                 315                 320

Lys Asp Phe Asn Thr Val Pro Tyr Ile Val Gly Ile Asn Lys Gln Glu
                325                 330                 335

Phe Gly Trp Leu Leu Pro Thr Met Met Gly Phe Pro Leu Ser Glu Gly
                340                 345                 350

Lys Leu Asp Gln Lys Thr Ala Thr Ser Leu Leu Trp Lys Ser Tyr Pro
                355                 360                 365

Ile Ala Asn Ile Pro Glu Glu Leu Thr Pro Val Ala Thr Asp Lys Tyr
                370                 375                 380

Leu Gly Gly Thr Asp Asp Pro Val Lys Lys Asp Leu Phe Leu Asp
385                 390                 395                 400

Leu Met Gly Asp Val Val Phe Gly Val Pro Ser Val Thr Val Ala Arg
                405                 410                 415

Gln His Arg Asp Ala Gly Ala Pro Thr Tyr Met Tyr Glu Phe Gln Tyr
                420                 425                 430

Arg Pro Ser Phe Ser Ser Asp Lys Lys Pro Lys Thr Val Ile Gly Asp
                435                 440                 445

His Gly Asp Glu Ile Phe Ser Val Phe Gly Phe Pro Leu Leu Lys Gly
                450                 455                 460
```

```
Asp Ala Pro Glu Glu Val Ser Leu Ser Lys Thr Val Met Lys Phe
465                 470                 475                 480

Trp Ala Asn Phe Ala Arg Ser Gly Asn Pro Asn Gly Glu Gly Leu Pro
                485                 490                 495

His Trp Pro Met Tyr Asp Gln Glu Glu Gly Tyr Leu Gln Ile Gly Val
            500                 505                 510

Asn Thr Gln Ala Ala Lys Arg Leu Lys Gly Glu Val Ala Phe Trp
        515                 520                 525

Asn Asp Leu Leu Ser Lys Glu Ala Ala Lys Pro Pro Lys Ile Lys
        530                 535                 540

<210> SEQ ID NO 2
<211> LENGTH: 34
<212> TYPE: DNA
<213> ORGANISM: Artificial Sequence
<220> FEATURE:
<223> OTHER INFORMATION: Synthetic DNA

<400> SEQUENCE: 2
gatatcccgg gcatatgtgg cttctcccgc tggt                        34

<210> SEQ ID NO 3
<211> LENGTH: 35
<212> TYPE: DNA
<213> ORGANISM: Artificial Sequence
<220> FEATURE:
<223> OTHER INFORMATION: Synthetic DNA

<400> SEQUENCE: 3
gcatcccggg aattctcaca gctcagcatg cttta                       35

<210> SEQ ID NO 4
<211> LENGTH: 31
<212> TYPE: DNA
<213> ORGANISM: Artificial Sequence
<220> FEATURE:
<223> OTHER INFORMATION: Synthetic DNA

<400> SEQUENCE: 4
gggcagccag cctcgccgcc tgttgtggac a                           31

<210> SEQ ID NO 5
<211> LENGTH: 31
<212> TYPE: DNA
<213> ORGANISM: Artificial Sequence
<220> FEATURE:
<223> OTHER INFORMATION: Synthetic DNA

<400> SEQUENCE: 5
tcacagctca gcatgcttta tcttgggtgg c                           31

<210> SEQ ID NO 6
<211> LENGTH: 23
<212> TYPE: DNA
<213> ORGANISM: Artificial Sequence
<220> FEATURE:
<223> OTHER INFORMATION: Synthetic DNA

<400> SEQUENCE: 6
agcctgcgct acggtagcga aac                                    23
```

<210> SEQ ID NO 7
<211> LENGTH: 22
<212> TYPE: DNA
<213> ORGANISM: Artificial Sequence
<220> FEATURE:
<223> OTHER INFORMATION: Synthetic DNA

<400> SEQUENCE: 7
tgaagggatc ctaagtaagt ag                                     22

<210> SEQ ID NO 8
<211> LENGTH: 32
<212> TYPE: DNA
<213> ORGANISM: Artificial Sequence
<220> FEATURE:
<223> OTHER INFORMATION: Synthetic DNA

<400> SEQUENCE: 8
aagctgaatt cgggcagcca gcctcgccgc ct                          32

<210> SEQ ID NO 9
<211> LENGTH: 33
<212> TYPE: DNA
<213> ORGANISM: Artificial Sequence
<220> FEATURE:
<223> OTHER INFORMATION: Synthetic DNA

<400> SEQUENCE: 9
gtcagtctag atcacagctc agcatgcttt atc                         33

<210> SEQ ID NO 10
<211> LENGTH: 33
<212> TYPE: DNA
<213> ORGANISM: Artificial Sequence
<220> FEATURE:
<223> OTHER INFORMATION: Synthetic DNA

<400> SEQUENCE: 10
aagctgaatt cgggcagcca gcctcgccgc ctg                         33

<210> SEQ ID NO 11
<211> LENGTH: 30
<212> TYPE: DNA
<213> ORGANISM: Artificial Sequence
<220> FEATURE:
<223> OTHER INFORMATION: Synthetic DNA

<400> SEQUENCE: 11
acctctagat actttatctt gggtggcttc                             30

<210> SEQ ID NO 12
<211> LENGTH: 31
<212> TYPE: DNA
<213> ORGANISM: Artificial Sequence
<220> FEATURE:
<223> OTHER INFORMATION: Synthetic DNA

<400> SEQUENCE: 12
acctctagat cactttatct tgggtggctt c                           31